US010849642B2

(12) United States Patent
Suzuki

(10) Patent No.: US 10,849,642 B2
(45) Date of Patent: Dec. 1, 2020

(54) ENDOSCOPE FORCEPS AND METHOD FOR PRODUCING ENDOSCOPE FORCEPS

(71) Applicant: Kaneka Corporation, Osaka (JP)

(72) Inventor: Nobuyuki Suzuki, Nagano (JP)

(73) Assignee: KANEKA CORPORATION, Osaka (JP)

( * ) Notice: Subject to any disclaimer, the term of this patent is extended or adjusted under 35 U.S.C. 154(b) by 220 days.

(21) Appl. No.: 16/017,632

(22) Filed: Jun. 25, 2018

(65) Prior Publication Data

US 2018/0303507 A1 Oct. 25, 2018

Related U.S. Application Data

(63) Continuation of application No. PCT/JP2016/083353, filed on Nov. 10, 2016.

(30) Foreign Application Priority Data

Dec. 25, 2015 (JP) .................................. 2015-254699

(51) Int. Cl.
*A61B 17/29* (2006.01)
*A61B 10/06* (2006.01)
*A61B 17/00* (2006.01)

(52) U.S. Cl.
CPC .............. *A61B 17/29* (2013.01); *A61B 10/06* (2013.01); *A61B 2017/0034* (2013.01); *A61B 2017/00438* (2013.01); *A61B 2017/00526* (2013.01); *A61B 2017/00845* (2013.01); *A61B 2017/2902* (2013.01); *A61B 2017/294* (2013.01);

(Continued)

(58) Field of Classification Search
CPC ... A61B 10/06; A61B 17/29; A61B 2017/294; A61B 2017/2947; A61B 2017/2902
See application file for complete search history.

(56) References Cited

U.S. PATENT DOCUMENTS

| 5,908,437 A | 6/1999 | Asano et al. |
| 6,309,404 B1 * | 10/2001 | Krzyzanowski ....... A61B 10/06 606/205 |
| 6,554,850 B1 | 4/2003 | Ouchi et al. |

FOREIGN PATENT DOCUMENTS

| JP | H10-118089 A | 5/1998 |
| JP | H10-179601 A | 7/1998 |
| JP | 2001-70309 A | 3/2001 |

(Continued)

OTHER PUBLICATIONS

International Search Report issued in International Application No. PCT/JP2016/083353, dated Jan. 10, 2017 (1 page).

*Primary Examiner* — Gregory A Anderson

(74) *Attorney, Agent, or Firm* — Osha Bergman Watanabe & Burton LLP

(57) ABSTRACT

An endoscope forceps includes a first forcep member and a second forcep member that are openably and closably joined to each other; a first operating member connected to a proximal side of the first forcep member; a second operating member connected to a proximal side of the second forcep member; a tubular member that fixes a proximal side of the first operating member and a proximal side of the second operating member; an outer tubular body formed of a flexible material; a traction line member; a first handle that is connected to a proximal side of the outer tubular body; and a second handle that is connected to the traction line member.

1 Claim, 5 Drawing Sheets

(52) U.S. Cl.
   CPC ............ *A61B 2017/2905* (2013.01); *A61B 2017/2947* (2013.01)

(56) References Cited

FOREIGN PATENT DOCUMENTS

| | | |
|---|---|---|
| JP | 2001-95807 A | 4/2001 |
| WO | 1997/024072 A1 | 7/1997 |

* cited by examiner

ENDOSCOPE FORCEPS AND METHOD FOR PRODUCING ENDOSCOPE FORCEPS

TECHNICAL FIELD

One or more embodiments of the present invention relate to an endoscope forceps to be used mainly for stanching in endoscopic surgeries or treatments.

BACKGROUND

Conventionally, forceps, which are instruments for holding tissues, have been used for taking tissues out of a body or stanching in endoscopic treatments. Besides the function as instruments for holding a target site or body tissues, the forceps can have a function as high-frequency instruments with their holding members connected to high-frequency power sources. Forceps have gone under various developments to prevent the operators from holding a wrong site other than a target site. Such developments include the improvement in the operability of the forceps and the simplification of the structures of the forceps.

For example, Patent Document 1 discloses an instrument for an endoscope, including: a rod in a longitudinal pipe, a forceps disposed near an end of the rod and having a pair of blades being rotatably held, and a wire attached to the end of the rod, in which each end of the wire is connected to the corresponding blade through an engaging hole in the blade. Patent Documents 2 and 3 disclose other types of bio-forceps for an endoscope. In these forceps, each operating wire in a sheath has a wire member at its end. An end of each wire member is bended in a loop and the looped end is engaged with the rear end part of the corresponding driving lever integrated with a forceps cup. In Patent Documents 2 and 3, two wire members for opening or closing the forceps are arranged in the sheath in the opening-and-closing direction of the forceps cup.

PRIOR ART DOCUMENTS

Patent Documents

PATENT DOCUMENT 1
  Japanese Unexamined Patent Application Publication No. 1110-118089
PATENT DOCUMENT 2
  Japanese Unexamined Patent Application Publication No. 2001-70309
PATENT DOCUMENT 3
  Japanese Unexamined Patent Application Publication No. 2001-95807

The instrument of Patent Document 1 has a possibility that the operability of the blades may be lowered for the following reason. When the forceps is opened too wide, the wire attached to the end of the rod comes into contact with the inner wall of the longitudinal pipe, which causes the displacement of the axis of the rod in the longitudinal pipe. In addition, since the wire should be inserted in the through hole in the rod, the instrument of Patent Document 1 is assembled in a complicated way. On the other hand, the bio-forceps of Patent Documents 2 and 3 can be assembled simply by fastening the two wire members using a fastening ring in the sheath. The bio-forceps of Patent Documents 2 and 3, however, has a possibility that the operability of the forceps may be lowered by the wire members coming into contact with each other at the opening or closing operation of the forceps.

One or more embodiments of the present invention provide an endoscope forceps that reduces the friction between the members used for the opening or closing operation to achieve a good operability while being able to be assembled in a simple way, and a method for producing the endoscope forceps.

SUMMARY

An endoscope forceps comprises: a first forcep member and a second forcep member that are openably and closably joined to each other; a first operating member connected to a proximal side of a center of the first forcep member; a second operating member connected to a proximal side of a center of the second forcep member; and a tubular member that fixes a proximal side of the first operating member and a proximal side of the second operating member; wherein a hypothetical plane including an opening-and-closing direction of the first forcep member and the second forcep member and a tube axial direction of the tubular member exists between the first operating member and the second operating member, the first operating member is placed at one side of the hypothetical plane in a proximal side of a proximal end of the first forcep member, and the second operating member is placed at the other side of the hypothetical plane in a proximal side of a proximal end of the second forcep member.

In the endoscope forceps according to one or more embodiments of the present invention, the proximal sides of the first and second operating members are fixed using the tubular member. This structure suppresses the first and second operating members from coming into contact with the inner walls of the forceps channel of an endoscope and an outer tubular body (described in detail below) disposed outside the tubular member, which suppresses the displacement of the axis of the forcep members. In one or more embodiments of the present invention, the first and second operating members are separated from each other with the hypothetical plane therebetween, in proximal sides of the proximal ends of the forcep members. This positional relationship suppresses the lowering of the operability due to the friction between the first and second operating members at an opening or closing operation. Compared with the conventional forceps of Patent Documents 2 and 3 in which the two wire members move in both the opening-and-closing direction of the forceps and the stacking direction of the forcep members in the opening or closing operation of the forceps, the first and second operating members according to one or more embodiments of the present invention move only in the opening-and-closing direction of the forceps in the opening or closing operation of the forceps. This simple movement of the operating members improves the transmission of torque.

In one or more embodiments, it is preferable that the first operating member and the second operating member are disposed inside the tubular member, and arranged in a direction perpendicular to both the opening-and-closing direction of the first forcep member and the second forcep member and the tube axial direction of the tubular member. This arrangement suppresses the first and second operating members from coming into contact with the inner walls of the forceps channel of an endoscope and the outer tubular body disposed outside the tubular member and the like, which suppresses the displacement of the axis of the forcep members.

In one or more embodiments, it is preferable that each of the first operating member and the second operating member has a parallel section in the proximal side thereof, the parallel sections are formed in parallel to each other, and each of the first operating member and the second operating member is bended to an opening direction of the first forcep member or the second forcep member in a distal side of the parallel section. Since the proximal sides of the first and second operating members are formed in parallel to each other, the first and second operating members hardly come into contact with the inner walls of the forceps channel of an endoscope and the outer tubular body disposed outside the tubular member and the like, which suppresses the displacement of the axis of the forcep members. Since the first and second operating members are bended respectively to the opening directions of the first and second forcep members in a distal side of the parallel sections, the forceps can be kept open without moving the operating members in the distal direction, which enables the operator to visually check a holding position and a holding angle easily.

In the conventional forceps of Patent Documents 2 and 3, when the wire members are pulled in the proximal direction to keep the forceps open, the wire members may get loosened or tensed and the torque from the proximal side may not be transmitted to the forcep members properly. On the other hand, in one or more embodiments, the preferable forceps according to one or more embodiments of the present invention can be kept open without any external power, and torque is transmitted properly.

In one or more embodiments, it is preferable that the first operating member and the second operating member are integrally formed in the proximal side thereof. In case of the first and second operating members integrally formed in the proximal sides, the positional relationship between these two operating members can easily be kept especially when the operating members in the tubular member are disposed.

In one or more embodiments, it is preferable that the first operating member and the second operating member are connected to a traction line member in the tubular member. This enables the first and second operating members to be moved in the tube axial direction for opening or closing the forceps.

One or more embodiments of the present invention include the endoscope forceps includes an outer tubular body that encloses the tubular member and distal sides of the first operating member and the second operating member. The outer tubular body, which encloses the distal sides of the first and second operating members and the tubular member, suppresses the tubular member from coming into contact with the inner wall of the forceps channel of an endoscope.

In one or more embodiments, it is preferable that each of the first operating member and the second operating member has at least one bending part, and a mountain fold of the bending part faces to an axial center of the tubular member. The bending parts of the first and second operating members help keep the forceps open without moving the operating members in the distal direction.

The forceps according to one or more embodiments of the present invention preferably further comprises a holding tube that holds the first forcep member and the second forcep member, and the distal sides of the first operating member and the second operating member are preferably protruded from a distal side opening of the holding tube. The holding tube fixes the positions of the first and second forcep members and prevents the first and second forcep members from being displaced in a predetermined direction (for exmaple in the tube axial direction). When the distal sides of the first and second operating members protrude from the distal side openings of the holding tube, the first and second forcep members can also protrude from the openings, which enables the forceps to open wide.

A method for producing an endoscope forceps, that comprises a first forcep member and a second forcep member that are openably and closably joined to each other, a first operating member connected to a proximal side of a center of the first forcep member, a second operating member connected to a proximal side of a center of the second forcep member, a traction line member connected to a proximal side of the first operating member or the second operating member, and a tubular member that fixes the proximal side of the first operating member and the proximal side of the second operating member, comprises the steps of; inserting a proximal side of the first operating member, a proximal side of the second operating member and a distal side of the traction line member into the tubular member; and fixing the first operating member and the second operating member to the tubular member while applying a stress to the first operating member and the second operating member in the opening direction of the first forcep member and the second forcep member. As described above, the method for producing the endoscope forceps according to one or more embodiments of the present invention includes a step for fixing the first and second operating members to the tubular member while applying a stress to the first and second operating members in the opening direction of the first and second forcep members. This step enables the first and second forcep members to be kept open without any external power. The forceps made in this method enables the operator to visually check a holding position and a holding angle easily, and transmits torque properly.

The endoscope forceps according to one or more embodiments of the present invention suppresses the first and second operating members from coming into contact with the inner walls of the forceps channel of an endoscope and an outer tubular body disposed outside the tubular member, which suppresses the displacement of the axis of the forcep members. One or more embodiments of the present invention also suppress the lowering of the operability due to the friction between the first and second operating members at an opening or closing operation.

The method for producing the endoscope forceps according to one or more embodiments of the present invention includes a step for fixing the first and second operating members to the tubular member while applying a stress to the first and second operating members in the opening direction of the first and second forcep members. This step enables the first and second forcep members to be kept open without any external power. The forceps made in this method enables the operator to visually check a holding position and a holding angle easily, and transmits torque properly.

Figure 1:
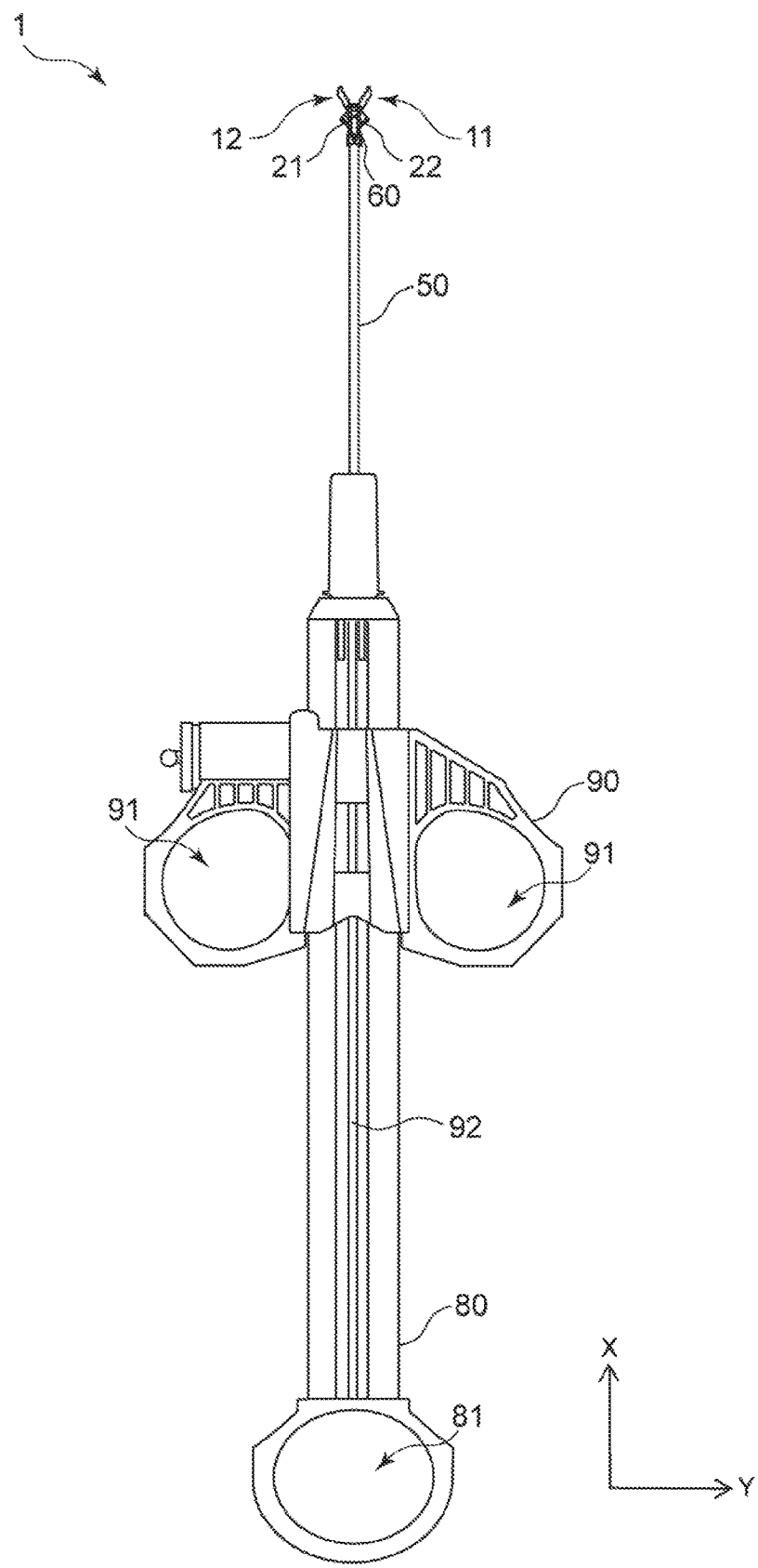
FIG. 1 is a plan view of an endoscope forceps according to one or more embodiments of the present invention.

One or more embodiments of the present invention will be specifically explained below based on the following embodiments, however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of one or more embodiments of the present invention.

1. Endoscope Forceps

An endoscope forceps is an instrument a part of which is inserted into a body through a forceps channel of the endoscope to hold and take out a target site such as body tissues or to stanch a target site in an endoscopic treatment. The endoscope forceps may simply be referred to as "forceps" in this specification.

Figure 2:
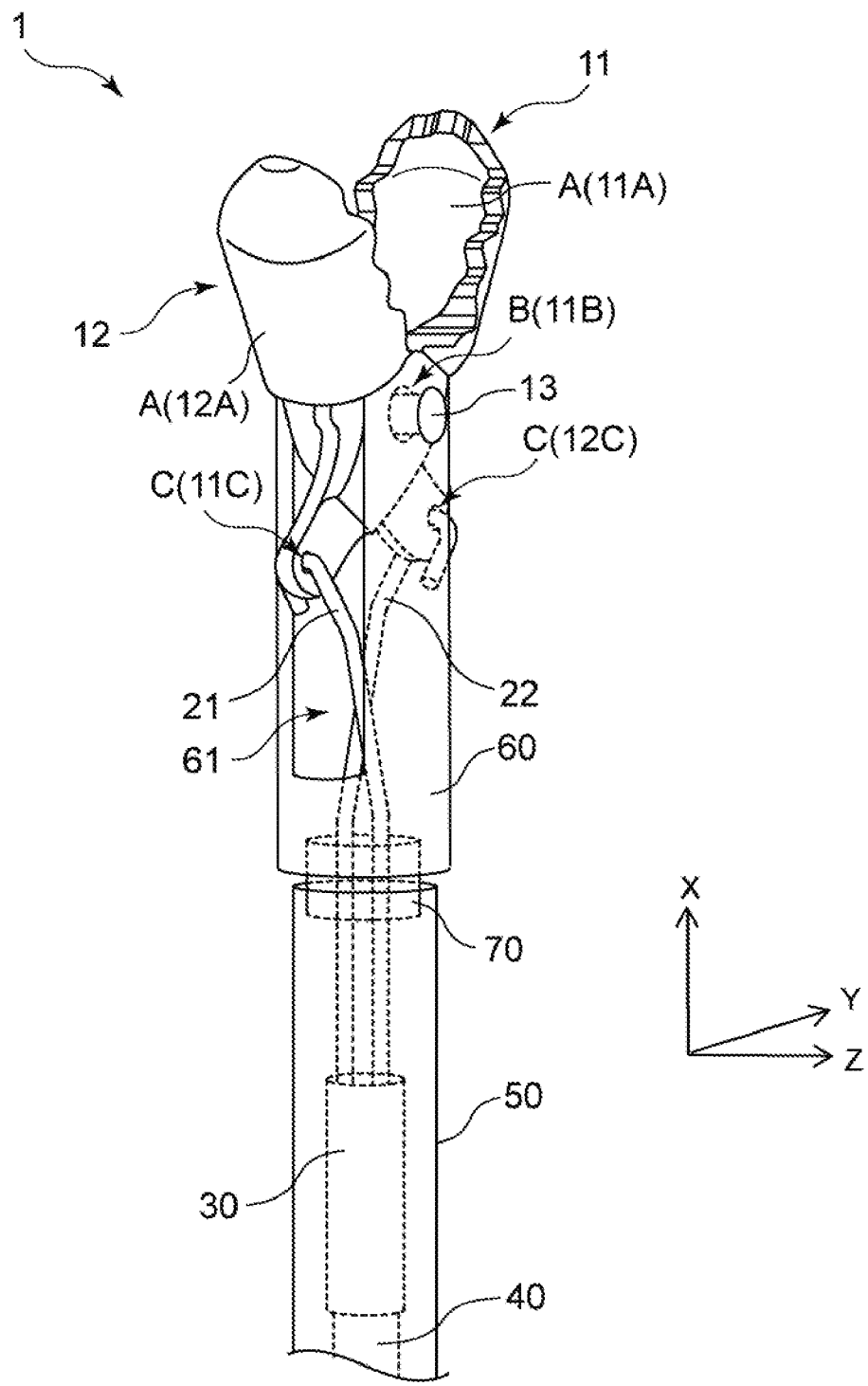
FIG. 2 is an enlarged perspective view of an endoscope forceps according to one or more embodiments of the present invention.
Figure 3:
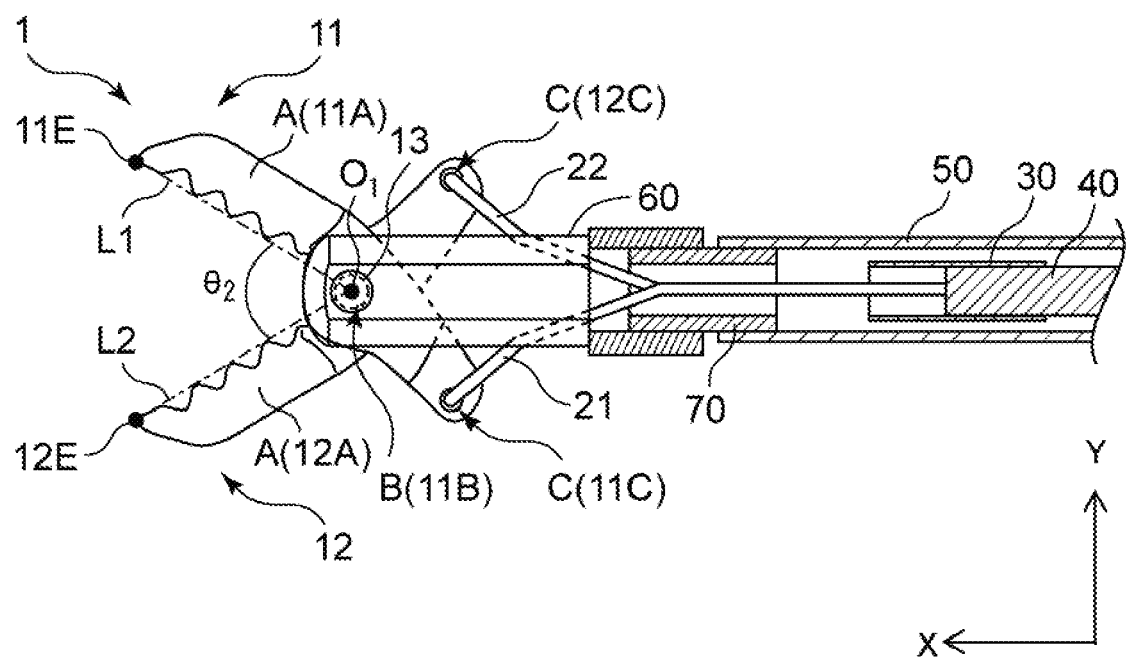
FIG. 3 is an enlarged plan view (a partial cross-sectional view) of an endoscope forceps according to one or more embodiments of the present invention.
Figure 4:
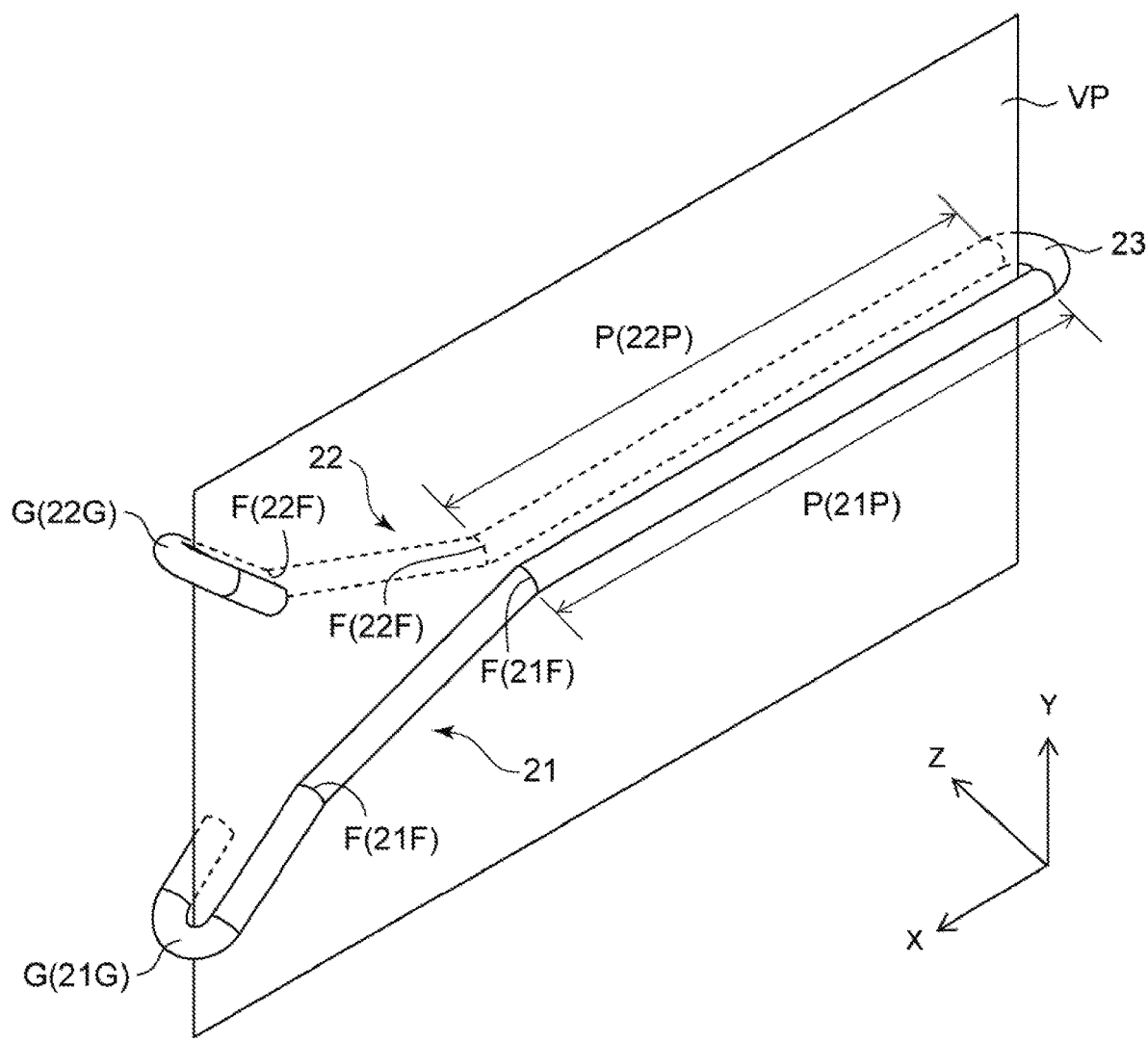
FIG. 4 is a perspective view of a first operating member and a second operating member according to one or more embodiments of the present invention.
Figure 5:
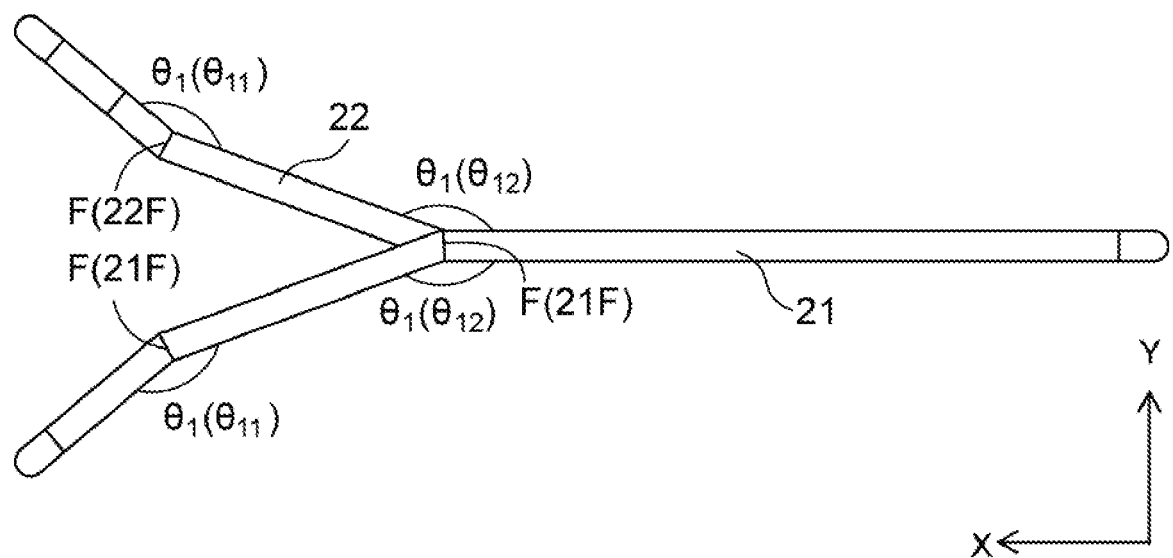
FIG. 5 is a plan view of a first operating member and a second operating member according to one or more embodiments of the present invention.
Figure 6:
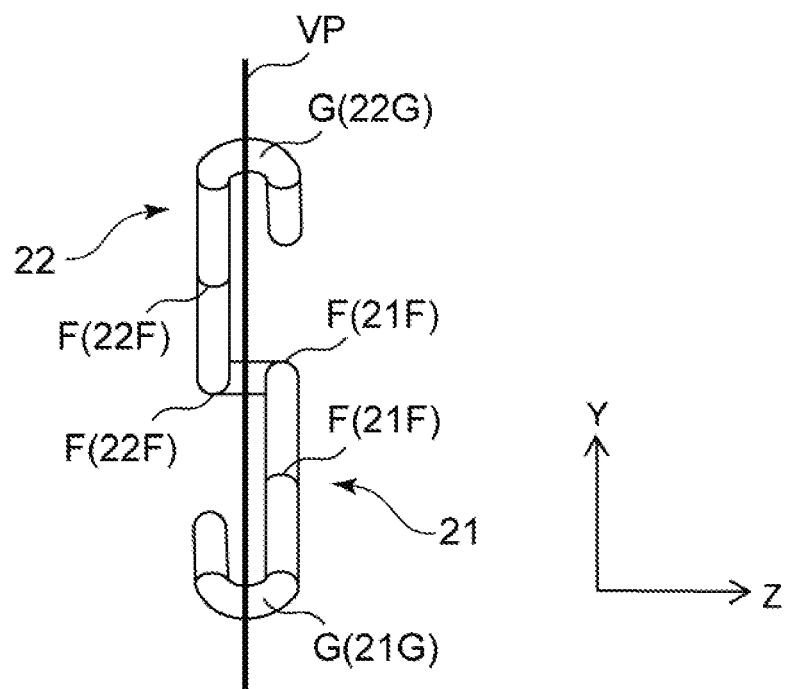
FIG. 6 is a side view of a first operating member and a second operating member according to one or more embodiments of the present invention.

The endoscope forceps according to one or more embodiments of the present invention will now be described with reference to FIGS. 1 to 6. FIGS. 1 to 3 are a plan view, an enlarged perspective view, an enlarged plan view (a partial cross-sectional view) of an endoscope forceps according to one or more embodiments of the present invention, respectively. FIGS. 4 to 6 are a perspective view, a plan view, a side view of a first operating member and a second operating member according to one or more embodiments of the present invention, respectively. As shown in FIGS. 2 and 3, the endoscope forceps 1 according to one or more embodiments of the present invention comprises a first forcep member 11 and a second forcep member 12 that are openably and closably joined to each other, a first operating member 21 connected to a proximal side of a center of the first forcep member 11, a second operating member 22 connected to a proximal side of a center of the second forcep member 12, and a tubular member 30 that fixes a proximal side of the first operating member 21 and a proximal side of the second operating member 22. As the first and second operating members 21 and 22 move in a tube axial direction of the tubular member, the first and second forcep members 11 and 12 gradually open or close with respect to each other to hold a target site such as mucous underlying tissues in a body for stanching, for example.

In one or more embodiments of the present invention, a proximal side of the tube axial direction of the tubular member 30 refers to a direction of an operator's hand side, while a distal side of the tube axial direction of the tubular member 30 refers to a direction opposite to the proximal side. A radial direction refers to a radial direction of the tubular member 30, and an inner side in the radial direction refers to a direction toward an axial center of the tubular member 30. In each drawing, an X-axis direction refers to the tube axial direction of the tubular member 30, and a Y-axis direction refers to the opening-and-closing direction of the first and second forcep members 11 and 12.

(1) Forcep Members

As shown in FIGS. 2 and 3, the forceps 1 has the first forcep member 11 and the second forcep member 12 that are openably and closably joined to each other with a pivot member 13 as their pivot. The first forcep member 11 and the second forcep member 12 may be referred to as "forcep members" as a whole hereinafter. The forcep members directly hold a target site such as body tissues. The forceps opens or closes as the first forcep member 11 and the second forcep member 12 rotate in the opposite directions to each other around the rotation axis where the forcep members are stacked and joined to each other.

Each of the forcep members 11 and 12 includes a holding part A, a coupling part B, and a connecting part C. The holding parts A mainly hold a target site. A holding part 11A of the first forcep member 11 faces a holding part 12A of the second forcep member 12.

In one or more embodiments, the holding parts A should preferably have a space inside for accommodating a target site. The holding parts A may be in the form of a cup with an inner space, blades, or a holding piece (a clip), for example. The holding parts A may have teeth to easily cut into a target site. The teeth of one holding part A engage with the teeth of the other holding part A. The teeth may be formed in the entire areas of the holding parts A, or only in the outer edges of the holding parts A as shown in FIG. 2. The shape of each tooth may be a polygonal shape such as a triangle shape, a rectangular shape, and a trapezoidal shape, or a shape combining some of these shapes. FIGS. 1 to 3 show an example in which the holding parts A are in the form of a cup. In one or more embodiments, the holding parts A should preferably be disposed at a distal side of the center of the forcep members.

The coupling parts B are used for coupling the forcep members with each other. Through the coupling parts B, the first forcep member 11 is coupled with the second forcep member 12 so that they can rotate in the opposite directions to each other. In FIGS. 2 and 3, the first forcep member 11 has a first through hole 11B as the coupling part B and the second forcep member 12 has a first through hole 12B (not shown) as the coupling part B. The first through hole 11B in the first forcep member 11 is aligned with the first through hole 12B in the second forcep member 12 in a direction perpendicular to both the opening-and-closing direction of the forceps 1 and the tube axial direction (in a stacking direction or a z-axis direction). The pivot member 13 is inserted in the first through holes 11B and 12B in the first and second forcep members 11 and 12 as the rotation axis.

The pivot member 13 may be any member to be inserted into the first through holes 11B and 12B in the forcep members 11 and 12, and may be a rivet for caulking, a screw, or a bolt, for example. In FIGS. 2 and 3, the pivot member 13 is a cylindrical rivet with a head and is inserted in the first through holes 11B and 12B in the first and second forcep members 11 and 12. The rivet is caulked and deformed at the head and the opposite end to couple the first forcep member 11 with the second forcep member 12.

In one or more embodiments, the coupling parts B should preferably be disposed in the proximal sides in terms of securing an enough axial length of the holding parts A. In one or more embodiments, the coupling parts B should preferably be disposed generally at the center in terms of improving the operability of the forceps 1.

The connecting parts C are connected to the operating members. In one or more embodiments, it is preferable that the first forcep member 11 is rotatably connected with the first operating member 21 and the second forcep member 12 is rotatably connected to the second operating member 22 through engagement, for example.

In one or more embodiments, each forcep member should preferably have a second through hole as the connecting part C for hooking a part of the corresponding operating member. In FIGS. 2 and 3, the first forcep member 11 has a second through hole 11C in the proximal side for hooking a part of the first operating member 21, and the second forcep member 12 has a second through hole 12C in the proximal side for hooking a part of the second operating member 22.

In one or more embodiments, in terms of stably operating the forceps 1, the connecting parts C should preferably be disposed to the proximal sides of the centers of the forcep members, more preferably in the most proximal areas of the four areas divided equally from the forcep members in the longitudinal direction.

Each forcep member may have a groove to engage with the contour of the corresponding operating member, to the proximal side of the connecting part C. The grooves in the forcep members, which accept parts of the operating members, suppress the operating members from being displaced with respect to the forcep members or from being unintentionally released from the forcep members.

In one or more embodiments, to enable the forceps 1 to open and close smoothly, the forcep members should preferably include the holding parts A, the coupling parts B, and the connecting parts C in this order from the distal sides.

The forcep members and the pivot member 13 may be composed of metal materials such as stainless steel and carbon steel, synthetic resin materials such as polyamide resins (e.g. nylon), polyolefin resins (e.g. polyethylene and polypropylene), polyester resins (e.g. PET), aromatic polyether-ketone resins (e.g. PEEK), polyimide resins, and fluoro-resins (e.g. PTFE, PFA, and ETFE).

(2) Operating Members

As shown in FIGS. 2 and 3, the forceps 1 includes a first operating member 21 connected to a proximal side of a center of the first forcep member 11, and a second operating member 22 connected to a proximal side of a center of the second forcep member 12. The first operating member 21 and the second operating member 22 may be referred to as "operating members" as a whole hereinafter. The operating members 21 and 22 are rod members for opening or closing the forcep members by traction. The operating members 21 and 22 may be metal wire rods, for example.

The outer diameter of the operating members may be determined in accordance with the diameter of the forceps channel of an endoscope, and may be 0.1 mm or more and 3 mm or less, for example. In one or more embodiments, to conform to the curves of organs or blood vessels in a body, the length of the operating members in the tube axial direction, that is the length of the operating members from the distal ends to the proximal ends should preferably be 20 mm or less, and more preferably 10 mm or less.

In one or more embodiments, the operating members should preferably be elastically deformable and be composed of highly elastic metal wire rods such as stainless steel and Ni—Ti alloys. The stainless steel may be SUS303 or SUS304, for example.

In one or more embodiments, to enable the forceps 1 to open wide, it is preferable that the operating members 21 and 22 are fixed to the tubular member 30 while a stress is applied to the operating members 21 and 22 in the opening direction of the forcep members.

As shown in FIG. 4, a hypothetical plane VP including an opening-and-closing direction of the first forcep member 11 and the second forcep member 12 and a tube axial direction of the tubular member 30 exists between the first operating member 21 and the second operating member 22 according to one or more embodiments of the present invention. The first operating member 21 is placed at one side of the hypothetical plane VP in a proximal side of a proximal end of the first forcep member 11, and the second operating member 22 is placed at the other side of the hypothetical plane VP in a proximal side of a proximal end of the second forcep member 12. Accordingly, the first operating member 21 and the second operating members 22 are separated from each other with the hypothetical plane VP therebetween, in proximal sides of the proximal ends of the forcep members. This positional relationship suppresses the lowering of the operability due to the friction between the first operating member 21 and the second operating member 22 at an opening or closing operation of the forceps 1.

In one or more embodiments, it is preferable that the first operating member 21 and the second operating member 22 are disposed inside the tubular member 30, and arranged in a direction (the Z-axis direction) perpendicular to both the opening-and-closing direction of the first forcep member 11 and the second forcep member 12 (the Y-axis direction) and the tube axial direction of the tubular member 30 (the X-axis direction). This arrangement suppresses the first and second operating members 21 and 22 from coming into contact with the inner walls of the forceps channel of an endoscope and the outer tubular body 50 disposed outside the tubular member 30 and the like, which suppresses the displacement of the axis of the forcep members.

In one or more embodiments, it is preferable that each of the first operating member 21 and the second operating member 22 has a parallel section P (21P and 22P) in the proximal side thereof, the parallel sections P are formed in parallel to each other, and each of the first operating member 21 and the second operating member 22 is bended to an opening direction of the first forcep member 11 or the second forcep member 12 in a distal side of the parallel section P. Since the proximal sides of the first and second operating members 21 and 22 are formed in parallel to each other, the first and second operating members 21 and 22 hardly come into contact with the inner walls of the forceps channel of an endoscope and the outer tubular body 50 disposed outside the tubular member 30 and the like, which suppresses the displacement of the axis of the forcep members. Since the first and second operating members 21 and 22 are bended respectively to the opening directions of the first and second forcep members 11 and 12 in a distal side of the parallel sections P, the forceps 1 can be kept open without moving the operating members in the distal direction, which enables the operator to visually check a holding position and a holding angle easily. In the conventional forceps of Patent Documents 2 and 3, when the wire members are pulled in the proximal direction to keep the forceps open, the wire members may get loosened or tensed and the torque from the proximal side may not be transmitted to the forcep members properly. On the other hand, in one or more embodiments, the preferable forceps according to one or more embodiments of the present invention can be kept open without any external power, and torque is transmitted properly. The first and second forcep members 11 and 12 may be bended to have bending parts as described below or be bended into curves.

In one or more embodiments, the length of the parallel sections P should preferably be 0.3 to 0.7 times the length of the operating members in the tube axial direction. In one or more embodiments, when the positions of the distal ends are considered as 0% and the positions of the proximal ends are considered as 100% in the operating members, the parallel sections P should preferably be disposed in the range of 30% to 100%, and more preferably in the range of 35% to 97%.

In one or more embodiments, to enable the tubular member 30 to properly enclose the first and second operating members 21 and 22, the proximal sides of the parallel sections P should preferably be fixed in the tubular member 30.

The operating members may be bended to the opening direction of the forcep members in a manner that each operating member is bended at least at one position as shown in FIGS. 2 to 5 or in a manner that each operating member is curved into an arc (not shown).

In one or more embodiments, to facilitate the manufacture of the operating members and to enable the forceps to open wide, each of the first and second operating members 21 and 22 should preferably have at least one bending part (referred to as "a first bending part" hereinafter) or more, and more preferably two or more first bending parts F, however, preferably have five or less first bending parts F, and more preferably four or less first bending parts F.

In one or more embodiments, it is preferable that a mountain fold of the bending part F faces to an axial center of the tubular member 30. The first bending parts F of the first and second operating members 21 and 22 help keep the forceps 1 open without moving the operating members in the distal direction. In one or more embodiments, the first bending parts F should preferably be bended along the opening-and-closing direction of the forcep members (the Y-axis direction).

In one or more embodiments, a first bending part 21F of the first operating member 21 and a first bending part 22F of the second operating member 22 should preferably be symmetric with respect to the hypothetical plane VP. This positional relationship enables the first and second operating members 21 and 22, which are moving in the axial direction, to timely come close to each other, which enables the stable opening or closing operation of the forceps 1.

The bending angle of the first bending parts F may be determined in accordance with the degree of opening or closing of the forceps. On the plane including the opening-and-closing direction of the forceps (the Y-axis direction) and the tube axial direction, the angle of the first bending parts F of the respective operating members is defined as a first bending angle $\theta_1$. In one or more embodiments, the first bending angle $\theta_1$ should preferably be 130° or more, more preferably 135° or more, much more preferably 140° or more, however, preferably 180° or less, more preferably 175° or less, much more preferably 170° or less.

As shown in FIGS. 2 to 5, when one operating member has two first bending parts F, each first bending angle $\theta_1$ should be in the above range. A first bending angle $\theta_{11}$ of one first bending part F (the first bending part F at the distal side, for example) may be equal to a first bending angle $\theta_{12}$ of the other first bending part F (the first bending part F at the proximal side, for example). In one or more embodiments, the first bending angle $\theta_{11}$ of the first bending part F at the distal side should preferably be larger than the first bending angle $\theta_{12}$ of the first bending part F at the proximal side. In one or more embodiments, the first bending angle $\theta_{11}$ of the first bending part F at the distal side should preferably be smaller than the first bending angle $\theta_{12}$ of the first bending part F at the proximal side. These angles of the bending parts may appropriately be determined in accordance with the size of a holding tube 60 or the forcep members.

In one or more embodiments, when one operating member has the two first bending parts F, the first bending parts F should preferably be disposed at the positions described below in terms of setting an appropriate degree of opening or closing of the forceps 1. In one or more embodiments, when the position of the distal end is considered as 0% and the position of the proximal end is considered as 100% in each operating member, one first bending part F should preferably be disposed in the range of 20% to 50%, and more preferably in the range of 30% to 40%. In one or more embodiments, the other first bending part F should preferably be disposed in the range of 5% or more and less than 20%, and more preferably in the range of 10% to 15%.

In one or more embodiments, the distal sides of the operating members should preferably be connected to the respective forcep members. Each forcep member has a second through hole C as the connecting part. As shown in FIGS. 4 and 6, the first operating member 21 has a second bending part G at the distal end part, and the second bending part G may be hooked in the corresponding second through hole C. In one or more embodiments, it is preferable that a part of the first operating member 21 extending from one end of a second bending part 21G is disposed along a first side of the hypothetical plane VP and the other part of the first operating member 21 extending from the other end of the second bending part 21G is disposed along a second side of the hypothetical plane VP. In addition, in one or more embodiments, it is preferable that a part of the second operating member 22 extending from one end of a second bending part 22G is disposed along the second side of the hypothetical plane VP and the other part of the second operating member 22 extending from the other end of the second bending part 22G is disposed along the first side of the hypothetical plane VP.

In one or more embodiments, as shown in FIG. 4, it is preferable that the first operating member 21 and the second operating member 22 are integrally formed in the proximal side thereof. In case of the first and second operating members 21 and 22 integrally formed in the proximal sides, the positional relationship between these two operating members can easily be kept especially when the operating members in the tubular member 30 are disposed.

The first and second operating members 21 and 22 are integrally formed with each other at the proximal sides by bending one metal wire rod generally at the center to form: a third bending part 23 generally at the center, the first operating member 21 extending from one end of the third bending part 23, and the second operating member 22 extending from the other end of the third bending part 23.

The forceps 1 according to one or more embodiments of the present invention can be used as a high-frequency stanching forceps. The forceps 1 according to one or more embodiments of the present invention can be used as a high-frequency stanching forceps (not shown) in which at least one of the first and second operating members 21 and 22 is configured to be connected to the positive electrode of a high-frequency power source and a return electrode to be attached to a human body is configured to be connected to the negative electrode of the high-frequency power source.

(3) Tubular Member

A tubular member 30 is a tube-shaped member, and fixes a proximal side of the first operating member 21 and a proximal side of the second operating member 22. The first and second operating members 21 and 22 are fixed to each other in an inner lumen of the tubular member 30. The tubular member 30 provided in this manner suppresses the first and second operating members 21 and 22 from being displaced with respect to each other in the tube axial direction of the tubular member. In one or more embodiments, the tubular member 30 should preferably tie the first and second operating members 21 and 22 in a bundle at the proximal sides to fix the first and second operating members 21 and 22. This further suppresses the first and second operating members 21 and 22 from being displaced with respect to each other in the tube axial direction.

The tubular member 30 may be composed of metal materials such as stainless steel or carbon steel, synthetic resin such as polyamide resin, polyester resin, polyolefin resin such as polyethylene. An inner diameter of the tubular member 30 may be larger than the sum of the outer diameter of the first operating member 21 and the outer diameter of the second operating member 22.

The tubular member 30 should have a length long enough to enclose at least the proximal end part of the first operating member 21 including its proximal side and the proximal end part of the second operating member 22 including its proximal side. In one or more embodiments, the axial length of the tubular member 30 should preferably be 0.05 or more times the length of the operating members in the tube axial direction, more preferably 0.1 or more times the length of the operating members in the tube axial direction, and much more preferably 0.15 or more times the length of the operating members in the tube axial direction, however, preferably 0.5 or less times the length of the operating members in the tube axial direction, more preferably 0.4 or less times the length of the operating members in the tube axial direction, and much more preferably 0.3 or less times the length of the operating members in the tube axial direction.

(4) Traction Line Member

In one or more embodiments, it is preferable that the first operating member 21 and the second operating member 22 are connected to a traction line member 40 in the tubular member 30. This enables the first and second operating members 21 and 22 to be moved in the tube axial direction for opening or closing the forceps 1. The operating members are connected to the traction line member 40 in the tubular member 30, and the tubular member 30 covers the connection of the operating members with the traction line member 40, which enables a smooth rotating operation of the forceps.

The traction line member 40 may be a metal wire rod composed of metal materials such as stainless steel and carbon steel, or a string composed of synthetic resins such as polyamide resins (e.g. nylon), polyolefin resins (e.g. polyethylene and polypropylene), polyester resins (e.g. PET), aromatic polyether-ketone resins (e.g. PEEK), polyimide resins, and fluoro-resins (e.g. PTFE, PFA, and ETFE). The string may be a mono filament, a multi filament, or a spun yarn.

The first and second operating members 21 and 22 may be connected to the traction line member 40 by mechanical fastening such as screwing or caulking, welding such as using laser or brazing, bonding using adhesives such as polyurethane-based adhesives, epoxy-based adhesives, cyano-based adhesives, or silicone-based adhesives. The operating members may be directly or indirectly connected to the traction line member 40. For example, the operating members and the traction line member 40 may separately be connected to the tubular member 30, which indirectly connects the operating members and the traction line member 40.

(5) Outer Tubular Body

The forceps 1 may further comprise an outer tubular body 50 that encloses the tubular member 30 and proximal sides of the first operating member 21 and the second operating member 22. The outer tubular body 50 prevents the traction line member 40 and the tubular member 30 from directly coming into contact with the inner wall of the forceps channel. In one or more embodiments, the outer tubular body 50 should desirably have both a flexibility to be bent along the shape of a body cavity and a rigidity to reach target tissues to be treated, in a balanced manner.

The outer tubular body 50 may be made of a coiled metal member or a coiled synthetic resin, a plurality of short cylindrical joint pieces rotatably connected in the axial direction, or a synthetic resin. In one or more embodiments, the outer tubular body 50 should preferably be made of transparent or translucent materials so that the operator can see the position of the traction line member 40 in the outer tubular body 50.

The outer tubular body 50 may be composed of the synthetic resin such as polyamide resins such as nylon, polyolefin resins such as polypropylene (PP), polyethylene (PE), polyester resins such as polyethylene terephthalate (PET), poly aromatic polyether ketone resins such as polyether ether ketone (PEEK), polyimide resins, fluorine-resins such as polytetrafluoroethylene (PTFE), tetrafluoro-ethylene-perfluoroalkylvinylether copolymer (PFA), ethylene-tetrafluoroethylene copolymer (ETFE).

A length of the outer tubular body 50 can be determined as 1.0 m to 2.5 m, for example, and an diameter of the outer tubular body 50 can be determined as 1.5 mm to 3.0 mm, for example.

(6) Holding Tube

In one or more embodiments, the forceps according to one or more embodiments of the present invention should preferably further comprise a holding tube 60 that holds the first forcep member 11 and the second forcep member 12. The holding tube 60 is a tubular member for suppressing the displacement of the rotation axis of the first and second forcep members 11 and 12 being rotated. The holding tube 60 accommodates at least parts of the first and second forcep members 11 and 12 in its inner lumen. In one or more embodiments, the holding tube 60 has a through hole formed in the direction different from the tube axial direction and preferably in the direction parallel to the stacking direction of the first and second forcep members 11 and 12. The pivot member 13 is inserted into the through hole in the holding tube 60, the through hole in the first forcep member 11, and the through hole in the second forcep member 12 to couple the holding tube 60, the first forcep member 11, and the second forcep member 12. The pivot member 13 in place suppresses the displacement of the rotation axis of the first and second forcep members 11 and 12 being rotated.

The shape of the holding tube 60 is not limited as long as it is a tubular shape, and may be a polygonal tubular shape, a circular tubular shape, or an elliptical tubular shape, for example.

The holding tube 60 may have openings 61 from which the forcep members and the operating members protrude. When the forcep members are rotated up to the maximum degree with respect to the tube axial direction to open the forceps 1 wide, the forcep members and the operating members protrude from the openings 61, which ensures a large range of movement of the forcep members and the operating members.

In one or more embodiments, to facilitate the opening and closing of the forceps 1, the openings 61 should preferably be formed in the holding tube 60 in parallel to the tube axial direction. In one or more embodiments, to prevent the holding tube 60 from impeding the opening or closing operation of the forceps 1, the openings 61 should preferably be formed in the distal side of the holding tube 60, and preferably in the distal end part of the holding tube 60 including its distal end.

In one or more embodiments, to enable both the first and second forcep members 11 and 12 to protrude from the holding tube 60, the holding tube 60 should preferably have two openings 61. In FIG. 3, the holding part 11A of the first forcep member 11, a connecting part 12C of the second forcep member 12, and the second operating member 22 protrude from one opening; and the holding part 12A of the second forcep member 12, a connecting part 11C of the first forcep member 11, and the first operating member 21 protrude from the other opening.

In one or more embodiments, it is preferably that the distal sides of the first operating member 21 and the second operating member 22 are preferably protruded from a distal side opening 61 of the holding tube 60. When the forcep members are rotated, the distal sides of the first and second operating members 21 and 22 protrude from the distal side openings 61 of the holding tube 60, which suppresses the distal sides of the operating members from coming into contact with the inner wall of the holding tube 60 and restricting the degree of opening of the forceps 1.

In one or more embodiments, to fix the positions of the coupling parts B of the forcep members in the tube axial direction, the holding tube 60 should preferably be connected to the distal side of the outer tubular body 50.

As shown in FIGS. 2 and 3, the holding tube 60 may be connected to the outer tubular body 50 using a tubular connecting member 70.

(7) Handle

As shown in FIG. 1, one or more embodiments of the present invention also include the forceps 1 including a first handle 80 connected to a proximal side of the outer tubular body 50 and a second handle 90 connected to a proximal side of the traction line member 40. The first handle 80 and the second handle 90 may be referred to as "handles" as a whole hereinafter. The operator holds the handles when opening or closing the forceps 1. The handles are connected to the proximal side of the outer tubular body 50.

When the forceps 1 is open, the second handle 90 is distal to the first handle 80. As the second handle 90 is moved in the proximal direction toward the first handle 80, the traction line member 40 moves in the proximal direction. The operating members connected to the traction line member 40 via the tubular member 30 also moves in the proximal direction. This makes the first and second operating members 21 and 22 come close to each other until the forceps 1 closes.

In one or more embodiments, the second handle 90 should preferably be disposed so that the second handle 90 moves in the tube axial direction with respect to the first handle 80. To suppress the displacement of the axis of the second handle 90 with respect to the first handle 80, the second handle 90 may have a guiding groove 92 extending in the tube axial direction to engage with the first handle 80 as shown in FIG. 1.

The size of the handles is not limited as long as the operator can properly hold them with one hand. The length of the handles may be 5 cm or more and 10 cm or less, and the maximum outer diameter of the handles may be 1 cm or more and 10 cm or less, for example.

To facilitate the holding of the handles, the handles may have an opening on which a finger is placed. In FIG. 1, the first handle 80 has an opening 81 and the second handle 90 has an opening 91.

The materials for the holding tube 60 and the handles may include synthetic resins such as ABS and polycarbonate, and foamed plastics such as polyurethane foam.

For connecting the outer tubular body 50 and the first handle 80, the traction line member 40 and the second handle 90, for example, mechanical fastening such as fitting, using screws, or caulking, welding such as using laser or brazing, bonding using adhesives such as polyurethane-based adhesives, epoxy-based adhesives, cyano-based adhesives, or silicone-based adhesives can be used.

2. Method for Producing Endoscope Forceps

A method for producing an endoscope forceps, that comprises a first forcep member and a second forcep member that are openably and closably joined to each other, a first operating member connected to a proximal side of a center of the first forcep member, a second operating member connected to a proximal side of a center of the second forcep member, a traction line member connected to a proximal side of the first operating member or the second operating member, and a tubular member that fixes the proximal side of the first operating member and the proximal side of the second operating member, comprises the steps of; inserting a proximal side of the first operating member, a proximal side of the second operating member and a distal side of the traction line member into the tubular member; and fixing the first operating member and the second operating member to the tubular member while applying a stress to the first operating member and the second operating member in the opening direction of the first forcep member and the second forcep member. The method for producing the forceps will now be described in detail. The individual members constituting the forceps have been described in "1. Endoscope Forceps" in this specification.

First, the first forcep member 11, the second forcep member 12, the first operating member 21, the second operating member 22, the traction line member 40, and the tubular member 30, all of which are necessary for producing the endoscope forceps 1, are prepared. The outer tubular body 50, the handles, and the holding tube 60, all of which have been described in "1. Endoscope Forceps", may be omitted. When the forceps includes some of these, however, those components are also prepared.

Then, the first forcep member 11 and the second forcep member 12 are stacked and openably and closably joined to each other.

When the forceps includes the holding tube 60, the first and second forcep members 11 and 12 are disposed in the holding tube 60 having a through hole.

The proximal side of the first operating member 21, the proximal side of the second operating member 22 and the distal side of the traction line member 40 are inserted into the tubular member 30 (Inserting Step). This temporarily determines the positions of the first operating member 21, the second operating member 22, and the traction line member 40 in the tube axial direction.

A proximal side of a center of the first forcep member 11 is connected to the first operating member 21, and a proximal side of a center of the second forcep member 12 is connected to a second operating member 22.

The first operating member 21 and the second operating member 22 are fixed to the tubular member 30 while applying a stress to the first operating member 21 and the second operating member 22 in the opening direction of the first forcep member 11 and the second forcep member 12 (Fixing Step).

With reference to FIG. 3, description will be made on how to apply a stress to the first forcep member 11 and the second forcep member 12. A line L1 connects a distal end 11E of the first forcep member 11 and a rotation center $O_1$ of the first forcep member 11, and a line L2 connects a distal end 12E of the second forcep member 12 and a rotation center $O_2$ (not shown) of the second forcep member 12. The angle between the line L1 and the line L2, which is inside in the radial direction of the forcep members, is defined as an opening angle $\theta_2$. The value of the angle $\theta_2$ is A1 under the condition that the forcep members are connected to the operating members and the operating members are not fixed to the tubular member 30. The first and second operating members 21 and 22 are fixed to the tubular member 30 at the angle of A2 (A1<A2) while applying a certain degree of stress to the first and second operating members 21 and 22 in the opening direction of the first and second forcep members 11 and 12. As a result of this fixing step, the first and second operating members 21 and 22 have a reaction in the closing direction of the first and second forcep members 11 and 12. When no external power is applied to the forceps, the value of the angle $\theta_2$ will be A3 (A1≤A3<A2). As described above, the method according to one or more embodiments of the present invention includes the fixing step, which keeps the opening angle $\theta_2$ of A2 (in an open state) without any external power being applied to the forceps. The forceps made in this method enables the operator to visually check a holding position and a holding angle easily, and transmits torque properly. The opening angle of the forceps can be adjusted by adjusting the value of the stress to be applied to the first and second operating members 21 and 22. The forceps 1 made in the method according to one or more embodiments of the present invention has the opening angle that facilitates the holding of a target site. The forceps 1 thus can suitably be used for an endoscope having a small diameter, for example, a diameter of approximately 2 cm.

In one or more embodiments, in the fixing step, a stress should preferably be applied to the first and second operating members 21 and 22 under the condition that the forceps 1 is open at the maximum degree. This enables the first and second forcep members 11 and 12 to be kept open without any external power.

In one or more embodiments, in the fixing step, the first and second operating members 21 and 22 should preferably be configured to have a reaction in the closing direction of the first and second forcep members 11 and 12. For this purpose, in one or more embodiments, the first and second operating members 21 and 22 should preferably be elastically deformable and be composed of highly elastic metal wire rods such as stainless steel and Ni—Ti alloys.

The first and second operating members 21 and 22 may be fixed to the tubular member 30 by mechanical fastening such as fitting, using screws, or caulking, welding such as using laser or brazing, bonding using adhesives such as polyurethane-based adhesives, epoxy-based adhesives, cyano-based adhesives, or silicone-based adhesives.

When the forceps 1 includes the outer tubular body 50, the proximal side of the traction line member 40 is inserted into the outer tubular body 50 through the distal side of the outer tubular body 50. The outer tubular body 50 thereby encloses the traction line member 40 together with the tubular member 30. The holding tube 60 may be connected to the outer tubular body 50 using the tubular connecting member 70 as shown in FIGS. 2 and 3.

When the forceps includes the handles, the first handle 80 is connected to the distal side of the outer tubular body 50 and the second handle 90 is connected to the distal side of the traction line member 40.

This application claims the benefit of the priority date of Japanese patent application No. 2015-254699 filed on Dec. 25, 2015. All of the contents of the Japanese patent application No. 2015-254699 filed on Dec. 25, 2015, are incorporated by reference herein.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

DESCRIPTION OF REFERENCE SIGNS

1: an endoscope forceps
11: a first forcep member
12: a second forcep member
A, 11A, 12A: a holding part
B, 11B, 12B: a coupling part (a first through hole)
C, 11C, 12C: a connecting part (a second through hole)
13: a pivot member
21: a first operating member
22: a second operating member
F, 21F, 22F: a first bending part
G, 21G, 22G: a second bending part
P, 21P, 22P: a parallel section
23: a third bending part
30: a tubular member
40: a traction line member
50: an outer tubular body
60: a holding tube
80: a first handle
90: a second handle
$\theta_1$, $\theta_1'$, $\theta_{12}$: a first bending angle
$\theta_2$: an opening angle
VP: a hypothetical plane

What is claimed is:
1. A method for producing an endoscope forceps, comprising:
    inserting a proximal side of a first operating member, a proximal side of a second operating member and a distal side of a traction line member into a tubular member; and
    fixing the first operating member and the second operating member to the tubular member while applying a stress to the first operating member and the second operating member in an opening direction of the first forcep member and the second forcep member,
    wherein the endoscope forceps comprises:
        the first forcep member and the second forcep member that are openably and closably joined to each other;
        the first operating member connected to a proximal side of the first forcep member;
        the second operating member connected to a proximal side of the second forcep member;
        the traction line member connected to the proximal side of the first operating member or the proximal side of the second operating member; and
        the tubular member that fixes the proximal side of the first operating member and the proximal side of the second operating member,
    wherein an angle A2 between the first forcep member and the second forcep member during the fixing is larger than an angle A3 between the first forcep member and the second forcep member after the fixing.

\* \* \* \* \*